US012467675B2

(12) United States Patent
Fullerton

(10) Patent No.: US 12,467,675 B2
(45) Date of Patent: Nov. 11, 2025

(54) COOLING MEDIA AND INSULATED COOLING SYSTEM

(71) Applicant: Equine Ice Right Systems LLC, Sulphur Springs, TX (US)

(72) Inventor: Kristine Marie Fullerton, Sulphur Springs, TX (US)

(73) Assignee: Equine Ice Right Systems LLC, Sulphur Springs, TX (US)

( * ) Notice: Subject to any disclaimer, the term of this patent is extended or adjusted under 35 U.S.C. 154(b) by 79 days.

(21) Appl. No.: 18/483,383

(22) Filed: Oct. 9, 2023

(65) Prior Publication Data

US 2024/0118012 A1 Apr. 11, 2024

Related U.S. Application Data

(60) Provisional application No. 63/378,947, filed on Oct. 10, 2022.

(51) Int. Cl.
*F25D 3/00* (2006.01)
*A61F 7/10* (2006.01)

(52) U.S. Cl.
CPC .......... *F25D 3/00* (2013.01); *A61F 2007/108* (2013.01); *F25D 2303/08221* (2013.01); *F25D 2303/085* (2013.01); *F25D 2331/8015* (2013.01)

(58) Field of Classification Search
CPC .. F25D 3/00; F25D 2303/08; F25D 2303/082; F25D 2303/0822;

(Continued)

(56) References Cited

U.S. PATENT DOCUMENTS 3,463,161 A * 8/1969 Stella ................. B65D 81/3895 126/400
4,240,436 A * 12/1980 Singleton .................. A61F 7/10 607/108

(Continued)

FOREIGN PATENT DOCUMENTS

EP 0046894 A1 * 3/1982 ............... A61F 7/00

OTHER PUBLICATIONS

Ice Horse, Ice Horse All Purpose Wrap, at least by Nov. 2023, Chewy.com, United States.

(Continued)

*Primary Examiner* — Joseph F Trpisovsky
(74) *Attorney, Agent, or Firm* — Timothy G. Ackermann

(57) ABSTRACT

A cold pack includes a sealed package containing liquid portion and a support structure, with the liquid portion formed of water and menthol isopropyl alcohol in a 4:1 ratio. The support structure is open-cell foam containing interconnected volumes retaining the liquid portion, with cells connected to one another by ligaments. A pack system supports one or more cold packs in pouches for application to a target. Pouches include an insulating layer and a mesh layer that sandwich two large sides of the cold packs, with the mesh layer adjacent to the target, and the insulating layer exposed to the environment. The mesh layer and the insulating layer have a high ratio of thermal conductivity. The pack system includes a waist strap for applying cooling to a human back or a rectangular form for forming into a cylinder-type shape for applying cooling to a horse's leg.

17 Claims, 7 Drawing Sheets

(58) Field of Classification Search
CPC ..... F25D 2303/08221; F25D 2303/085; F25D 2331/8015; A61F 2007/108; A61F 2007/0024; A61F 2007/0027; A61F 2007/0029; A61F 2007/0039; A61F 2007/0043; A61F 2007/0231; A61F 7/02; A61F 7/10
See application file for complete search history.

(56) References Cited

U.S. PATENT DOCUMENTS

| | | | | |
|---|---|---|---|---|
| 5,120,587 | A | 6/1992 | McDermott, III | |
| 7,240,513 | B1 * | 7/2007 | Conforti | A45C 13/02 62/457.2 |
| 2002/0052569 | A1 * | 5/2002 | Horning | A61F 7/10 602/41 |
| 2009/0163984 | A1 * | 6/2009 | Robinson | A61F 7/02 607/114 |
| 2016/0332419 | A1 | 11/2016 | Calkins | |
| 2018/0133050 | A1 * | 5/2018 | Manning | A61F 7/02 |
| 2021/0100681 | A1 * | 4/2021 | Miles | A61F 5/4404 |
| 2021/0128170 | A1 * | 5/2021 | Wada | A61F 7/007 |
| 2023/0280077 | A1 * | 9/2023 | Dziedzic | A45C 3/001 62/457.1 |

OTHER PUBLICATIONS

Rester's Choice, Rester's Choice Flexible Resuable Cold and Hot Pack, at least by Nov. 2023, Walmart.com, United States.

Dura-Tech, Dura-Tech Neoprene Ice Boot (full leg), at least by Nov. 2023, Sstack.com, United States.

* cited by examiner

COOLING MEDIA AND INSULATED COOLING SYSTEM

REFERENCE TO RELATED APPLICATIONS

This application claims priority to U.S. Ser. No. 63/378,947 and incorporates that application in its entirety.

FIELD OF THE INVENTION

Cooling media to be cooled or frozen for later use in cooling horses, humans, and other mammals, and insulating and support systems for insulating the cooling media and holding the cooling media in place to cool horses, humans, and other mammals. Cooling may also be applied for purposes of therapy.

BACKGROUND OF THE INVENTION

Mammals such as horses and humans generate heat internally and frequently need to shed excess heat to the environment. When the environment or other circumstances make that difficult, mammals can become uncomfortable and even suffer heat stress and heat strokes. Such factors and circumstances include high temperatures, exposure to the sun, exertion, and clothing, or equipment (such as saddles, body armor) that limit the shedding of heat.

Mammals and other animals may be treated using cold therapy (cryotherapy) on portions of the target's anatomy, principally on soft tissues (including muscles, tendons, ligaments, fascia), such as to reduce inflammation.

Applying a cold or frozen media to the target can help shed that excess heat and/or provide cold therapy. Such media may be contained in packs to facilitate application, handling, and freezing. Such packs may be supported by a pack system to hold the cold pack, containing the cold or frozen media, close to the target's skin (and near the soft tissue desired to be cooled). The cold pack is colder than the external surface of the target (typically skin) and thus heat energy transfers from the target to the cold pack by heat transfer mechanisms, including radiation, convection, and conduction.

A pouch may insulate the cold pack to prolong the cold or frozen state of the media and the cold packs and improve the cooling rate to the target. Insulation can also improve the efficiency of the effective heat transfer, the amount of the heat absorbed that is from the target, and not the environment. The pack system may support one or more pouches.

BRIEF STATEMENT OF THE INVENTION

A cooling media comprises a liquid portion and a support structure for the liquid portion.

A liquid portion can comprise a mixture of 1.5 parts water::1 part 50% menthol isopropyl alcohol, or a mixture of 4 parts water::1 part menthol isopropyl alcohol (100%). The menthol isopropyl alcohol may include methyl salicylate. In the context of "liquid portion" the term "liquid" does not refer to whether it has become a liquid or partially liquid or frozen or partially frozen (i.e. as a result of a phase change). The specific proportion of 4::1 creates a viscosity providing favorable malleability when the pack has been kept in a home freezer for sufficient time and also holds colder temperatures for extended times. That favorable malleability is believed to result, in part, from the alcohol lowering the freezing point to at or around the temperature reached by ordinary home freezers (around −4° F. or around −20° C.) such that the liquid portion does not fully freeze but remains malleable. Proportions similar to 4::1 may be operable under similar circumstances.

A support structure can comprise material that contains interconnected volumes or cells to retain the liquid portion, including sponge, spongy foam, or open-cell foam. The foam or sponge or other material forming the support structure may be a unitary, single, piece, or may be multiple smaller pieces, e.g. a set of elongated parallel pieces, to allow easier bending of the cold pack to form around a targeted area (e.g. human neck, horse's leg, etc.). An example of a support structure is polyurethane craft foam. Thickness examples are 1" and 0.75" and 0.5". Another example of a support structure is synthetic sponge. Those interconnected cells act to support the liquid portion and limit its movement even when the liquid portion is in a liquid or partially liquid phase. The support structure is also flexible and permits the liquid portion to be molded/bent even when the liquid portion is in a frozen (solid) or partially solid phase. This is believed to be in part because the support structure includes cells that are partly open, and contain volumes of the liquid portion but partly separate the volume in one cell from the volume in another cell. Further, the cells are connected to one another by ligaments that are normally formed of the same material as the cells which are flexible and permit cells limited motion relative to one another (even when those cells contain solid or partially solid liquid portion). Thus, the support structure both limits movement of the liquid phase and permits motion of the solid phase.

A cold pack comprises one or more cooling media and a package enclosing those one or more cooling media. The packaging may be a plastic, heat-sealable package with a high proportion of air removed therefrom the loaded package, e.g. by using a vacuum sealer, before the package is heat-sealed. This results in the cold pack containing substantially only the liquid portion and the support structure. The support structure allows the cold pack to maintain its shape even as the liquid portion thaws. Maintaining its shape, and limiting movement of the liquid phase (or the solid phase) of the liquid portion, helps keep the cooling effects of the cold pack evenly distributed.

The ability of the cold pack to maintain its shape and the low amount of air within the cold pack helps permit construction of larger cold packs. The packs and corresponding pouches may vary in sizes, with cold packs sized so that a pouch holding a single cold pack is approximately 5-8% larger in outer measurements than the cold packs. Larger dimensions help the cold packs provide longer cooling effects without being bulky or cumbersome. Cold packs range in size from around 7×8×½ inches to 11×12×¾ inches, to 6×22×1 inches, and other sizes. Cold packs may be made with non-symmetrical sides as fits the need. Thus, other size ranges include a 10.5×15 inch rectangle with one corner removed to form a 7 inch top edge and a 8 inch angle, with a 1 inch thick support structure of 9.5×12 inch rectangle with one corner removed to form a 4.5 inch top edge and a 7 inch angle. Cold packs are low-profile and have two large sides and four (or more) substantially smaller edges (recognizing that they are not exactly rectangular in section along their full lengths/widths). Thus, the vast majority of their surface area is one or the other of the two large sides. Timed temperature trials showed that a cold pack having a larger contiguous volume (>10 oz.) of liquid portion stays cold up to 100% longer than those having smaller volumes (<8 oz.).

A pouch may insulate the cold packs to also improve the efficiency of the effective heat transfer from the target and/or improve the cooling rate applied to that target. As the exterior surface of the target is typically skin, and the cold pack may be at or below 0° F., it is desirable not to permit the cold pack to touch the target surface. Thus, the pouch also acts to space the cold pack from that target surface.

A pouch may comprise of an insulating layer and a mesh layer, where the mesh layer and insulating layer are intended to sandwich (lay adjacent to) the two large sides of one or more cold packs. The mesh layer is the side of the pouch that is applied to a target (interior), while the insulating layer is exposed to the environment (directly, or indirectly via a pack system if present) (exterior). Thus, heat flow is designed and desired to flow from the target, through the mesh layer, and into the cooling media (at its interior side) within the pouch. But heat will also flow (undesirably) from the environment, via a pack system (if present), through the insulating layer, and into the cooling media (at its exterior side) within the pouch. Thus, a high ratio of thermal conductivity (low ratio of thermal resistance) between the mesh layer and the insulating layers is desirable. A high thermal conductivity of the mesh layer helps the cooling rate, and a low thermal conductivity of the insulating layer helps prolong the cooling ability of the cold pack. The mesh layer and the insulating layer are each also low-profile and have two large sides and four much smaller edges. The mesh layer and the insulating layer may be joined together at their edges by known methods, such as sewing. One or more edges may be left open (or with flap or similar closable opening) to permit insertion and removal of the cold pack.

A mesh layer may comprise a layer of a rubberized mesh or a perforated mesh. This mesh can take the form of a checkerboard pattern, in which there are alternating open sections (or openings) and closed sections and the closed sections are connected to one another by grid. The openness of the mesh layer may be expressed as a percentage of the combined open sections to entire surface (i.e. the grid and open and closed sections combined). The openness of the mesh layer may be around 30%, 35%, 38%, 40%, 43%, 45%, 50%, 55%, or 60%. The closed sections of the mesh layer are (desirably) insulating to insulate the target surface from the cold pack. The mesh thickness (measured at the closed sections) may be around 2/32, 3/32, or 4/32 (1/16, 3/32, 1/8) of an inch. Open sections may be described by their aperture size which may be around 15, 20, 25, 30, 35, 40, 45 mils each. For a mesh layer of about 40% or 43% openness, the open sections' aperture size may be around 2/16×2/16 inches, 2/16×3/16 inches, 3/16×3/16 inches, or rectangular or square and about 0.0156, 0.0234, or 0.0353 square inches (15.6, 23.4, or 35.3 mils), and the closed sections may be around 2/16×3/16 inches, 3/16×3/16 inches, 3/16×4/16 inches, or rectangular or square and about 0.0234, 0.0353, or 0.0469 square inches (23.4, 35.3, or 46.9 mils).

Examples of such rubberized mesh comprise non-adhesive/non-slip foamed surface coverings, such as shelf or drawer liners. One type of mesh layer comprises of a knitted polyester scrim featuring a coating of thermally foamed polyvinyl chloride (PVC) resin. The knitted construction of the scrim provides an arrangement of woven yarns defining a pattern of apertures that correspond to a configuration of openings extending through the thickness of the cured PVC material. Alternatively, the PVC resin may be knife coated to either side of a knitted scrim devoid of openings, or to a non-woven fabric of autogenously bonded fibers, producing a continuous layer of supported foam. The PVC compound also includes a plasticizer that imparts a removable nonslip mechanical bond between the foamed covering and an applied surface. One type of mesh layer comprises of a scrim having a plurality of spaced frame elements. The frame elements include alternating spanned frames and fully-open frames. A foamed material surrounds the frame elements covering the spanned frames with support pillows formed by the foam and substantially leaving open the fully-open frames to form open sections (openings). Thus, the foam material comprises support pillows which substantially close alternate openings to give a checkerboard configuration mesh layer. The support pillows may be spongy, pliable and resilient and may be formed of PVC, food-grade EVA, or other suitable thermoplastic or reactive plastic foams.

The mesh layer may have a relatively high thermal conductivity overall. This is believed to result from the high openness of the mesh layer and the large open section size. A 40% openness of, for example, does provides support pillows that insulate the target surface from direct contact with the cold pack's package and greatly limits conduction therebetween. But the 40% open area formed open sections of about 25 mil each in a checkerboard pattern permits more airflow between the cold pack exterior and thus more efficient convection therebetween, and permits more efficient radiant heat transfer by exposing the cold pack to the target surface. Similar results would apply in similar fashion to different mesh layers with differing openness.

The insulating layer may comprise a high-resistance layer sandwiched between two fabric layers. The fabric layers may comprise substantially waterproof or water-resistant fabric such as nylon ripstop fabric with a rubber backing or duck canvas. The high-resistance layer may comprise composite materials such as reflective foam core insulation or bubble foil insulation or other aluminum foil bubble composites. Such insulation includes air bubble insulation containing one or two or more layers of air bubble material (which may be formed of PVC) sandwiched between exterior layers bonded to the air bubble material, where those layers are low-emissivity, and may be plastic and may be white or may metallized on their exterior sides or may be a metallic foil material. A composite, sandwich plate formed of multiple layers can have improved bending resistance. of sandwiched materials An example of such a high-resistance layer is foil/bubble radiant barrier insulation, which is flexible to bend around a body or leg, but also can provide stiffness transverse to a direction of curvature once curved. That is, bending the insulation into a cylinder-type shape lends stiffness/bending resistance along the axis of the cylinder. Thus, such radiant barrier insulation provides vertical stability, such as supporting the weight of pouches holding cold packs arranged vertically, such as in a horse boot. The horse boot being self-supporting (and avoiding slumping) improves contact of the cooling structure with the target. Such radiant barrier insulation also provides stability of form for other pack systems & pouches used for horse blankets, human backpacks, dog harnesses, horse hoods, human neck packs, etc. A high-resistance layer of this type may have an R-value/in. of about 1 to 3. A high-resistance layer may be formed of neoprene, fiberglass insulation, or wool batting, which may offer similar insulating properties. But these alternatives do not provide the structural stability to the pouches that the radiant barrier insulation does.

This high-resistance layer acts as a high resistance insulating element for purposes of both conductive heat transfer (the bubbles contain air acting as insulation) and radiant heat transfer (radiation) (as the white surface and especially the foil or metallic layer act as a radiant barrier). The fabric layers may be joined together at their edges by known methods, such as sewing to enclose the high-resistance layer.

The insulated pouches proved to increase the longevity of the cold temperatures by about 100%. Cold packs of 24 oz.

inside a pouch maintained cold temperatures for over two hours when placed on 130° surfaces, in direct sun, with outside temperatures over 100°.

Embodiments of the invention include: A cold pack, for being cooled and used to cool other materials, comprising: one or more cooling media, and a package retaining said one or more cooling media; the one or more cooling media each comprising a support structure and a liquid portion; the liquid portion comprising a mixture of about 4 parts water::1 part isopropyl alcohol. Embodiments of the invention include: the support structure comprising one or more pieces of material containing interconnected volumes, and the material containing interconnected volumes comprising cells that are partly open and that partly separate the volume in one cell from the volume in another cell, and where the support structure may be composed of sponge, spongy foam, open-cell foam, polyurethane craft foam, and/or synthetic sponge. Embodiments of the invention include: the cold pack comprising a plurality of cooling media retained in the package and comprising a plurality of support structures, where the liquid portion is in communication with each of said plurality of support structures. Embodiments of the invention include the cooling media remaining malleable when said liquid portion is frozen.

Embodiments of the invention include: A pack system for supporting and applying a cooling device, comprising: one or more pouches; each of the pouches comprising a mesh layer and an insulating layer. Embodiments of the invention include: the insulating layer comprising: two layers of fabric, and a high-resistance layer interposed between said two fabric layers, and the insulating layer comprising: a composite material comprising metallic foil and bubble insulation, or at least one layer of a bubble material sandwiched between exterior layers having a low emissivity, or two layers of a bubble material sandwiched between said exterior layers comprising metallic foil. Embodiments of the invention include: the mesh layer comprising a layer of a rubberized mesh, the rubberized mesh comprising alternating open sections closed sections, and a grid; and the grid connecting the closed sections to one another, the mesh layer having an openness of between 30% to 60%, and the mesh layer comprising a polyester scrim coated with thermally-foamed PVC. Embodiments of the invention include: the pack system comprising a pouch opening and a cold pack supported in said pouch opening, and also comprising four or more pouches, said pouches arranged in a grid. Embodiments of the invention include: the pack system comprising hook-and-loop fasteners for wrapping said pack system around the leg of a horse, or the pack system comprising one pouch and an elastic band joined to said pouch by an attachment, comprising hook-and-loop fasteners.

A pack system may both help maintain one or more pouches containing cold packs supported thereby in a desired position on a target (e.g. horse, human). The pack system may support one or more pouches by known methods, including hook and loop attachment, sewing, buckles, etc. Pack systems may be horse horse boots, sheets, horse neck wraps, horse headstalls, dog harnesses, or elastic back and neck wraps for humans. Horse boots are placed around the bottom of a horse's leg and foot (not under the hoof) and extend upward around 12", 18", 24" or 36".

Making the pouch may comprise hook and loop fasteners sewn onto the fabric layers if and where needed, then the two fabric layers are sewn together on three sides, together with the mesh layer on one side of the two fabric layers. The high-resistance layer is inserted between the two fabric layers and the fabric layers are then sewn together to enclose the high-resistance layer therein with some air space permitted between the fabric layers and the high-resistance layer. The fourth side of the mesh layer may be left open (or closably open) to receive and retrieve the cold pack from the pouch. The completed pouch can then be used as either a stand alone cooling unit, or as part of a pack system. If the latter, the pouch or pouches may be attached to structures by known methods, including hook and loop attachment, sewing, buckles, snaps, etc., and maintained in position using closures (including hook and loop attachment, buckles) and elastic, neoprene (e.g. if sewn to the fasteners) and the like. Such structures include, but are not limited to, horse boots, horse sheets, horse blankets, horse neck wraps, horse headstalls, dog harnesses, or elastic back and neck wraps for humans, attachments to horse halters and bridles, attachments to dog collars and harnesses, mats in dog kennels, blankets for livestock (goats, sheep, cattle, pigs), and coverings for rabbit and poultry crates.

Uses of the cold packs include fast cooling for home kitchen use, to quickly cool foods and beverages, and cooling and maintaining cold foods and beverages in personal portable coolers. Uses of the pack systems including cold packs include: targeted, secure cooling for horses, including legs, back, neck, head, etc. for the purposes of therapy and/or comfort; targeted, secure cooling for dogs, including body, limbs, chest, neck, etc. for the purposes of therapy and/or comfort; targeted, secure cooling for livestock, including limbs, body, head, and neck for the purposes of therapy and/or comfort; targeted, secure cooling for humans including head, core, back, neck, face, and/or individual joints on arms, legs, hands, and feet for the purpose of therapy, cosmetics, and/or comfort; cooling mats for kennel trays for animals; cooling pads for the tops of wire kennels/cages for animal occupant cooling; personal cooling device as personal protective equipment (PPE); and fast, secure cooling for animals experiencing heat stress.

DETAILED DESCRIPTION OF THE INVENTION

Figure 1A:
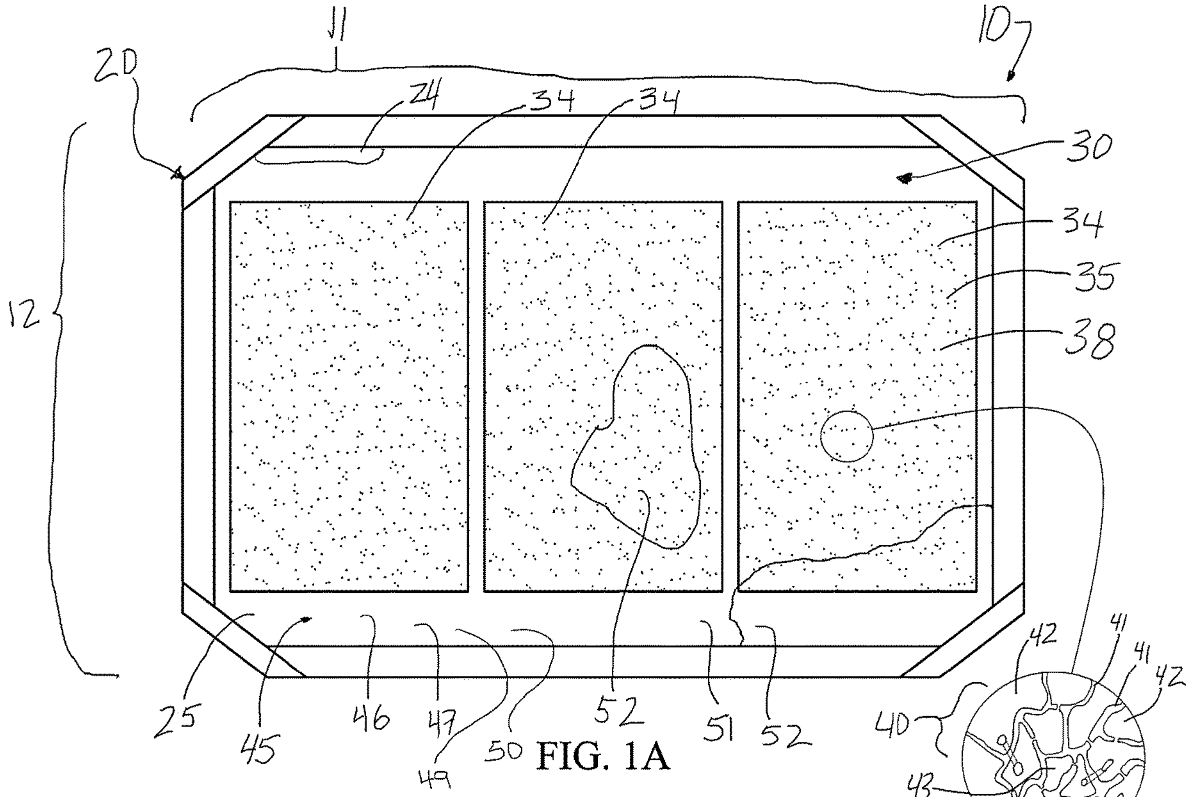
FIGS. 1A & 1B show front views of embodiments of a cold pack of the invention.

Referring to FIG. 1A, in an embodiment of the invention, cold pack 10 includes three cooling media 30 and package 20 enclosing those cooling media 30. Package 20 is a heat-sealed, flexible plastic package, resulting in a low-profile cold pack 10 size of about 7"×8.5" (length 11×width 12) and around 0.5" in thickness (depth 13). Different plastic films 25 suitable for heat-sealing may be used, including biaxially-oriented polyethylene terephthalate film, including such film that has been metalized by vapor deposition that is known as metalized polyester. A loaded package 20 is sealed using a vacuum to remove a high proportion of air 24 before heat sealing. Each of cooling media 30 includes liquid portion 45 and support structure 34. Support structures 34 are foam 35 pieces of material 38 of about 1.9"×7.25"×0.5" arranged side-by-side lengthwise and contain interconnected volumes 40 or cells 42 (having volumes 43) to retain liquid portion 45. Support structures 34, in another embodiment, are sponges 35. Liquid portion 45 is 12.5-12.8 oz. of mixture 46 of 1.5 parts water 47::1 part 50% menthol isopropyl alcohol 49 and may include methyl salicylate 50. Liquid portion 45 may exist in either liquid phase 51, solid phase 52, or both. Some portion of liquid portion 45 is outside support structure 34 and some is within support structure 34. Within support structure 34, liquid portion 45 is in interconnected volumes 40 or cells 42, with interconnections 44 permitting liquid portion 45 to pass therebetween. Cells 42 are connected to one another by ligaments 41 formed of the same material as cells 42 and which are flexible and permit cells 42 limited motion relative to one another.

Figure 1B:
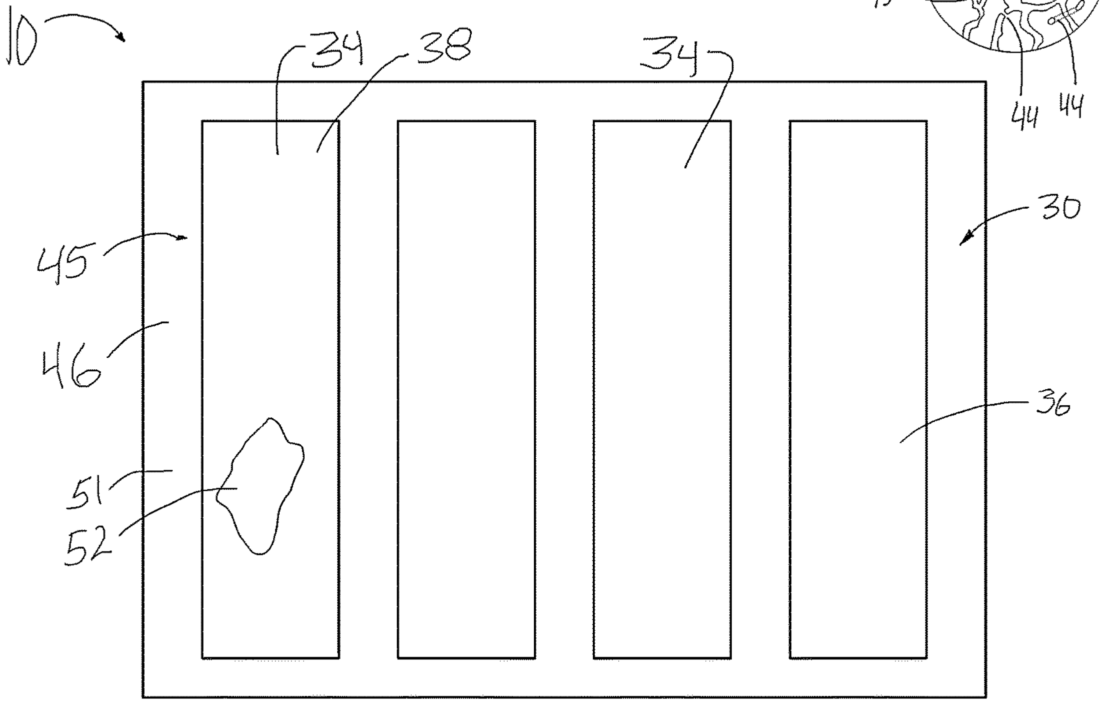

Referring to FIG. 1B, in an embodiment of the invention, cold pack 30 includes four cooling media 30 and package 20 enclosing those cooling media 30. Package 20 is a heat-sealed, flexible plastic package, resulting in a low-profile cold pack 10 size of about 7"×8.75" (length 11×width 12) and around 1.5" in thickness (depth 13). Loaded package 20 is sealed as above for FIG. 1A. Each of cooling media 30 includes liquid portion 45 and support structure 34. Support structures 34 are foam 35 pieces of material 38 about 1.5"×6"×1.5" arranged side-by-side lengthwise, and contain interconnected volumes 40 or cells 42 (having volumes 43) to retain liquid portion 45. Liquid portion 45 is 11.5 oz. of mixture 46 as above for FIG. 1A. Some portion of liquid portion 45 is outside support structure 34 and some is within support structure 34.

Figure 2A:
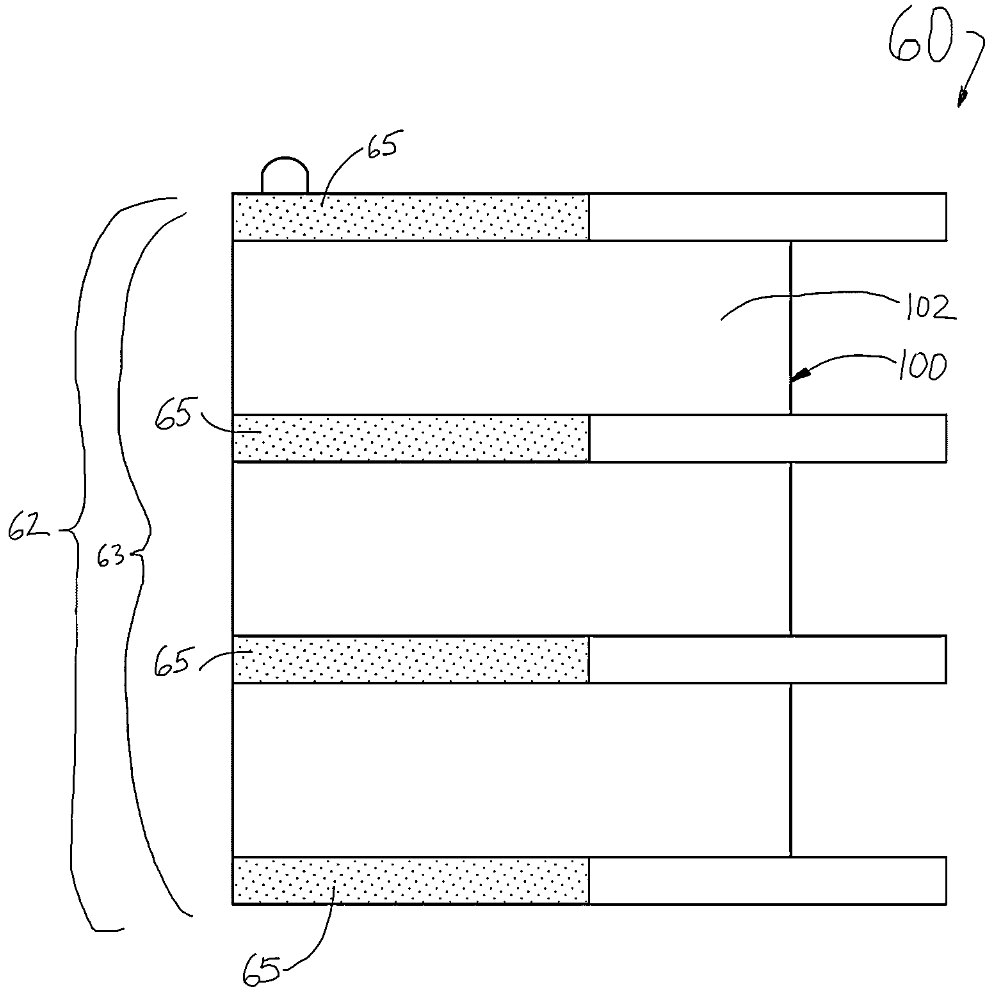
FIGS. 2A & 2B show a front view and a rear view of an embodiment of a pack system of the invention with detail on FIG. 2B.
Figure 2B:
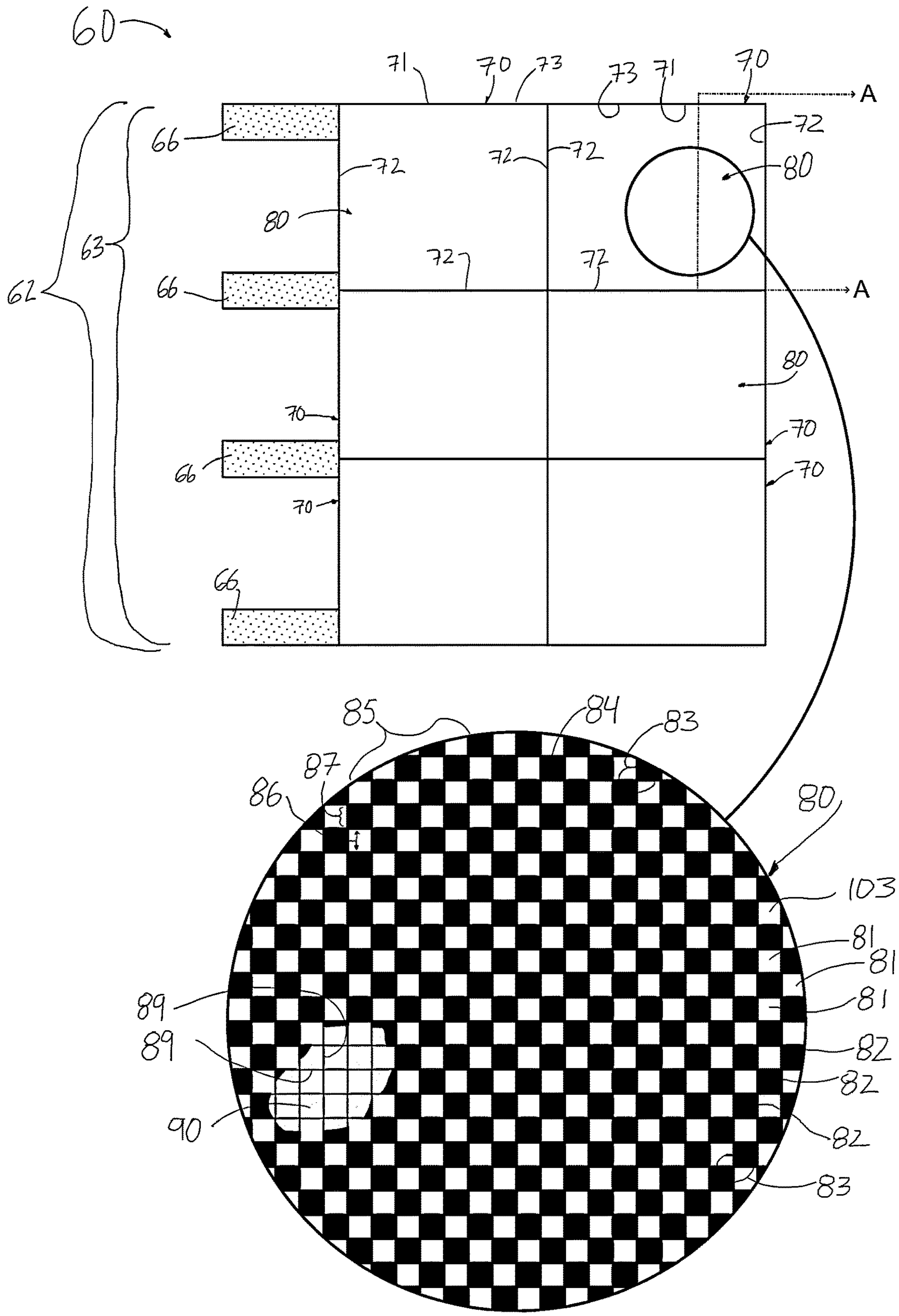
Figure 2C:
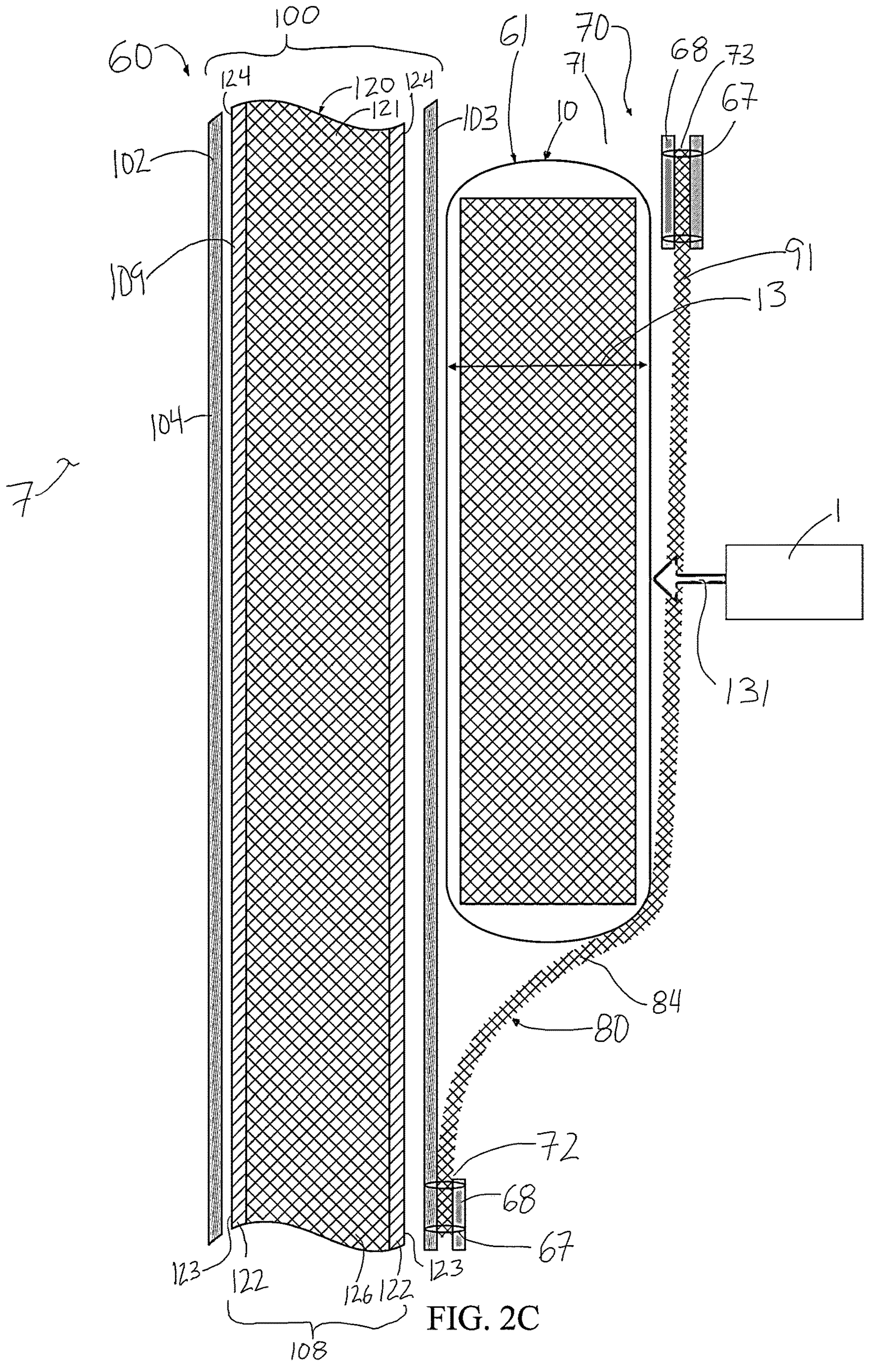
FIG. 2C is a cross-sectional view along lines A-A in FIG. 2B.

Referring to FIGS. 2A-2C, and to cold packs 10 in FIGS. 1A & 1B, in an embodiment, pack system 60 is for use for wrapping the bottom of leg 5 (and foot) of horse 4 (or some other target 1) and includes six pouches 70 adjacent to one another in a vertical 3×2 arrangement and cooling device 61. That six-pouch 70 part of the pack system 60 is about 14" high by 18" wide. Pouches 70 include insulating layer 100 and mesh layer 80, where mesh layer 80 and insulating layer 100 sandwich the two large sides (i.e. length 11/width 12) of cold pack 10 set therebetween and that is sized to fit within six pouch openings 71. For each pouch 70, mesh layer 80 and insulating layer 100 are joined together at closed edges 72 by sewing mesh 80 to fabric layer 103 via stitching 67 and using reinforcement layer 68. Open edge 73 of mesh layer 80 is at the top and is left open (unsewn) to permit insertion and removal of cold pack 10 from between mesh layer 80 and insulating layer 100, but has reinforcement layers 68 sewn to mesh 80 via stitching 67.

Insulating layers 100 of pouches 70 are formed as one structure. Insulating layers 100 include high-resistance layer 108 sandwiched between first and second fabric layers 102, 103. High-resistance layer 108, having thermal conductivity 109, is composite material 120 and is formed by sandwich plate 121. Sandwich plate 121 includes bubble insulation 126 (e.g. a one- or two-layer air bubble section) that has exterior layers 124 of metallic foil 122 on the exterior of bubble insulation 126. Multiple layers of composite material 120 promotes stiffness 128. Metallic foil 122 are low-emissivity layers 123. Each of fabric layers 102, 103 include nylon ripstop fabric with rubber backing 104.

Mesh layers 80, attached to insulating layers 100, are segmented to form six discrete pouch openings 71, one for each pouch 70. Mesh layer 80 is formed of rubberized mesh 84 made of non-adhesive/non-slip foamed surface covering, such as thermally-foamed PVC 90 on scrim 89 (shown in partial cutaway). Mesh layer 80 has thermal conductivity 91. Mesh 84 has the form of a checkerboard pattern, in which there are alternating open sections 81 (or openings) and closed sections 82, and closed sections 82 are connected to one another by grid 83 (see detail of FIG. 2B). The relative sizes/configuration of open sections 81, closed sections 82, and grid 83 define openness 85, aperture size 86, and closed section size 87.

Figure 3:
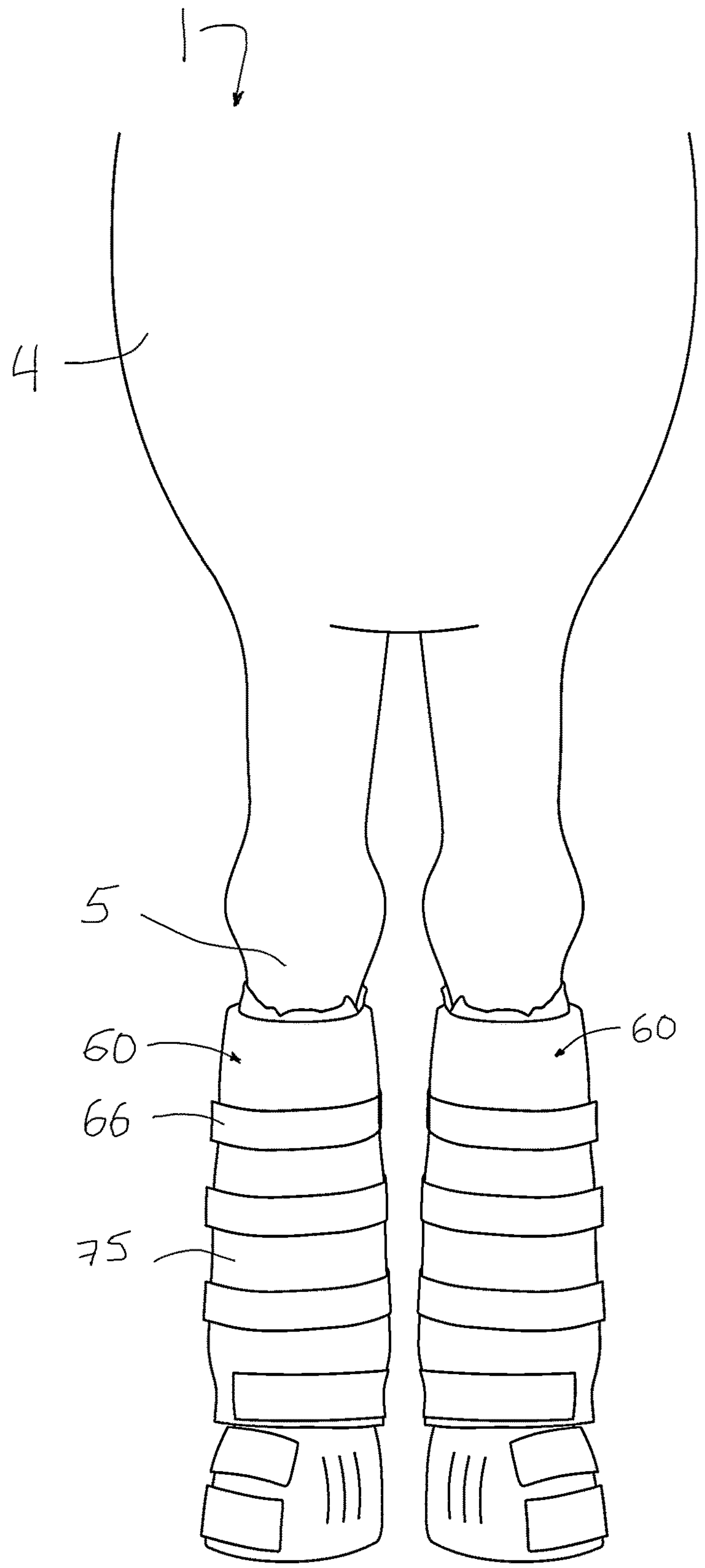
FIG. 3 shows a front view of the device of FIGS. 2A-2C in use.

Mesh layer 80 is sewn to form the arrangement of six discrete pouch openings 71 for holding cooling device 61. Cooling device 61, in this embodiment is multiple cold packs 10. Pouches 70 are formed with three closed edges 72 of each pouch opening 71 sewn to fabric layer 103, with the fourth as open edge 73. High-resistance layer 108 is inserted between fabric layers 102, 103, and those fabric layers are then sewn together to enclose high-resistance layer 108 therein. Closure 62, as hook and loop fasteners 63, are sewn onto fabric layer 102 that is opposite mesh layer 80, with hook end pieces 65 facing outwards (FIG. 2A) and exposing loop end straps 66 facing inwards (FIG. 2B) to permit pack system 60 to be wrapped and secured around leg 5 of horse 4, thus taking on a cylinder shape 75. Thus, mesh layer 80 is the side of pouch 70 that is applied to target 1 (the horse's leg/foot) while insulating layer 100 is exposed to environment 7 indirectly via pack system 60, as shown in FIG. 3. Desirably, thermal conductivity ratio 130, between thermal conductivity 91 of mesh layer 80 and thermal conductivity 109 of insulating layer 100 is large. Thus, heat flow 131 is designed and desired to flow primarily from target 1, through mesh layer 80, and into cooling media 30 (at its interior face 31) within pouch 70, and not from environment 7 and through insulating layer 100, and into cooling media 30 (at its exterior face 32).

Figure 4A:
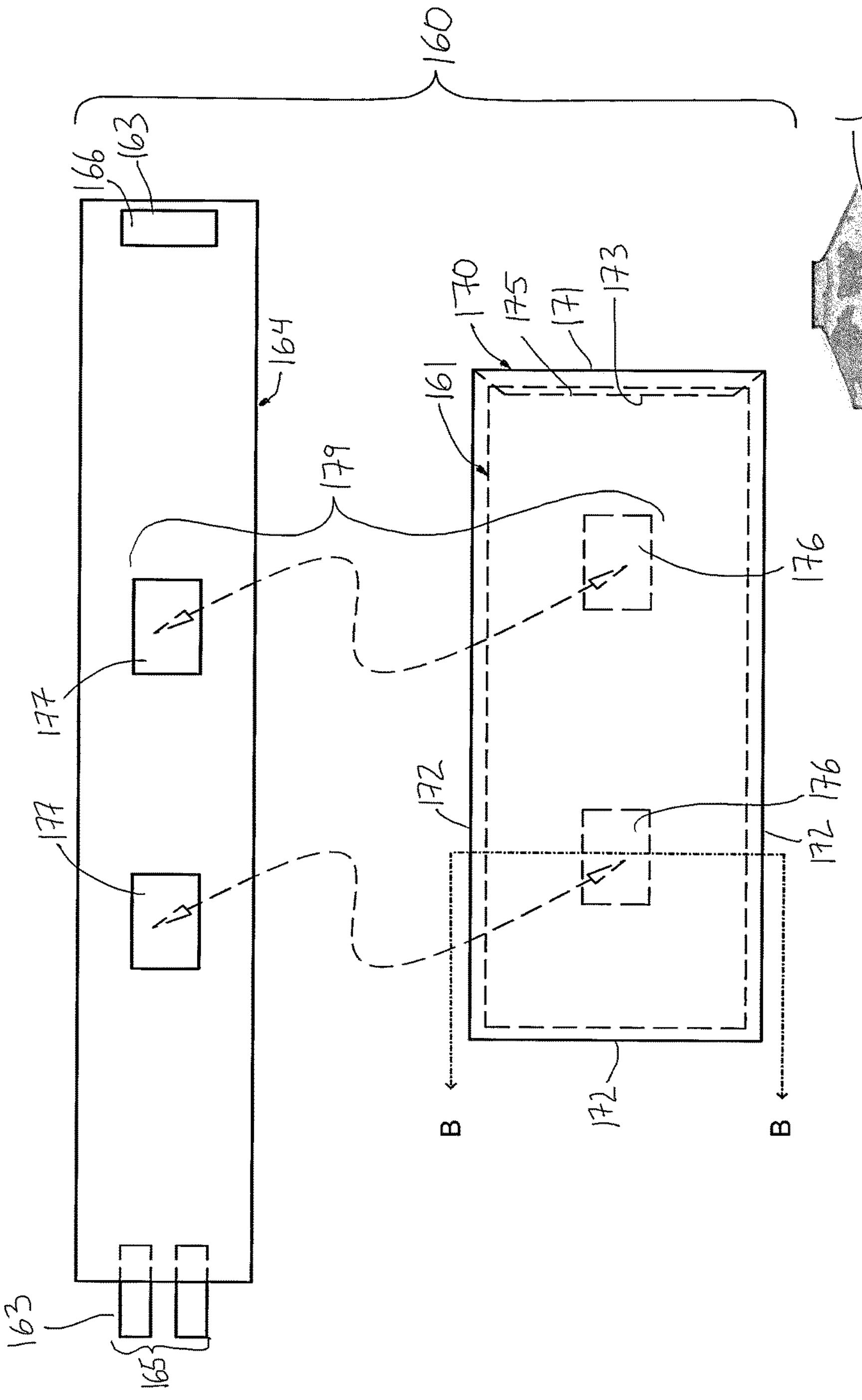
FIG. 4A shows a front view of an embodiment of a pack system of the invention.
Figure 4C:
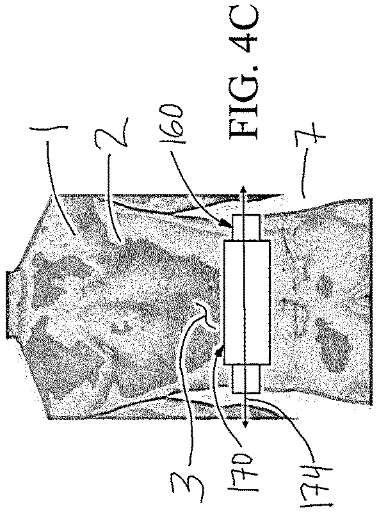
FIG. 4C shows a front view of the device of FIGS. 4A-4B in use.
Figure 4B:
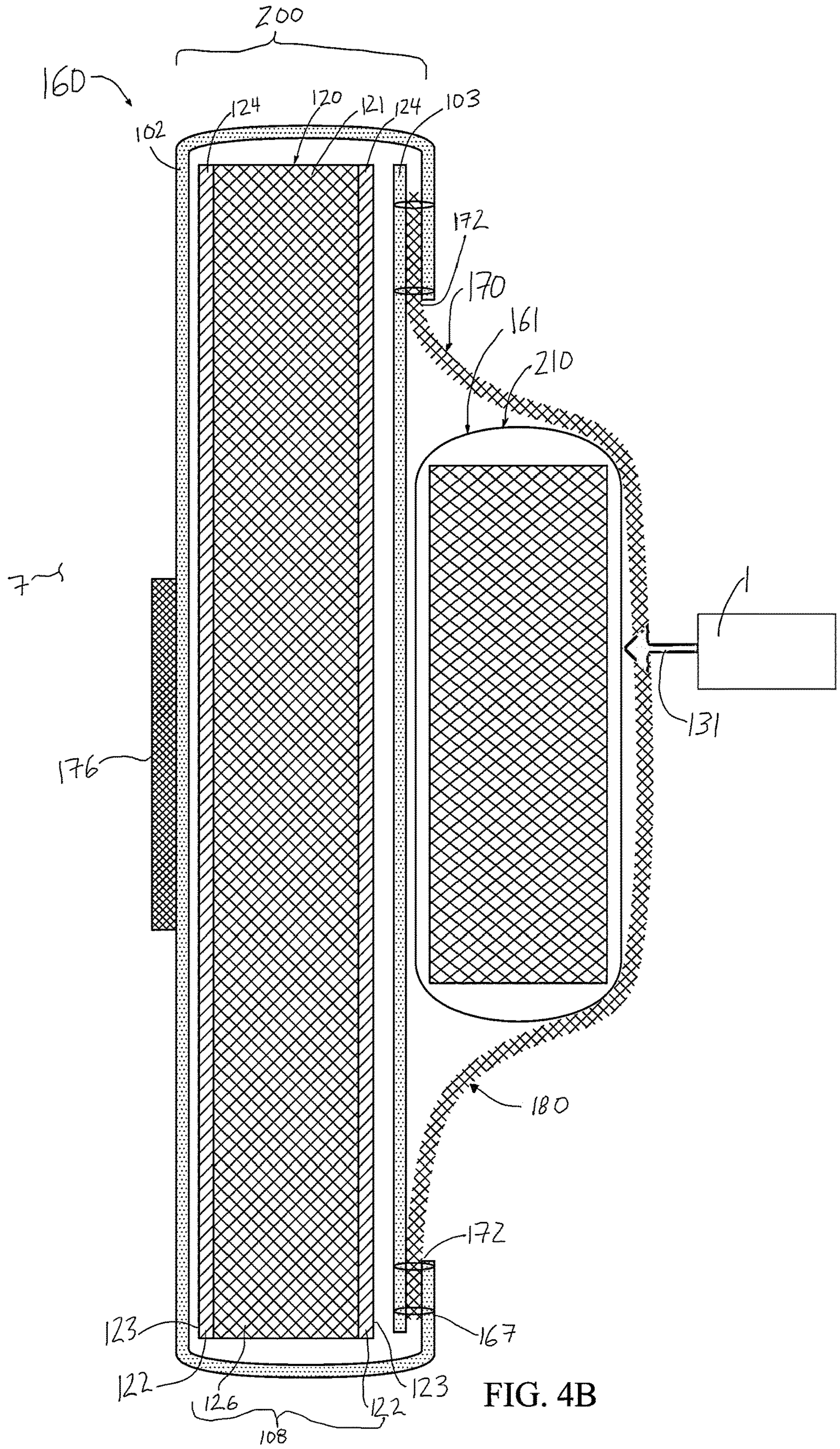
FIG. 4B is a cross-sectional view along lines B-B in FIG. 4A.

Referring to FIGS. 4A, 4B, & 4C, in an embodiment, pack system 160 for use for wrapping back 3 of human 2 includes one pouch 170 for holding cooling device 161, pouch 170 in a configuration having long axis 174 running laterally, around back 3, and elastic strap (or strap) 164 connected to pouch 170 via hook-and-loop fastener pouch attachment 179. That pouch 170 part of pack system 160 is about 7.5" high by 23" wide. Pouch 170 includes insulating layer 200 and mesh layer 180. Mesh layer 180 and insulating layer 200 sandwich the two large sides of cooling device 161. In this embodiment, cooling device 161 is cold pack 210 set therebetween, where cold pack 210 is about 6.5" high by 22" wide. Cold pack 210 is formed similarly to cold pack 10. Mesh layer 180 and insulating layer 200 are joined together at closed edges 172 via stitching 167. One short open edge 173 of mesh layer 180 is left open and closure 175 is provided to permit insertion and removal of cold pack 210 from between mesh layer 180 and insulating layer 200.

Insulating layer 200 is formed similarly to insulating layer 100.

Mesh layer 180 is formed similarly to mesh layer 80 (see detail of mesh layer 80 on FIG. 2B). Mesh layer 180 forms one discrete pouch opening 171 for one pouch 170. That pouch opening 171 can comprise substantially all of one open edge 173 of pack system 160, and permit cold pack 210 of similar dimensions to be inserted therein, being retained by closed edges 172.

High-resistance layer 108 is inserted between fabric layers 102, 103 and those layers enclose high-resistance layer 108 therein. Mesh layer 180 is sewn into fabric layer 103 to form discrete pouch opening 171 for holding cold pack 210, with three closed edges 172 sewn to fabric layer 103, with fourth open edge 173 left open. Closure 175 permits temporary closure and opening of open edge 173. Pouch attachment 179 includes two hook end patches 176 sewn onto the outer side of fabric layer 102 opposite mesh layer 180 with hook end patches 176 facing outwards.

Pack system 160 also includes elastic strap 164 with hook-and-loop fasteners 163 for supporting pack system 160 on human 2. Hook-and-loop fasteners 163 include loop end pieces 166 on one end of strap 164 matching hook end pieces 165 facing inwards and opposing loop end pieces 166 on the other end. Attachment 179 for pouch 170 includes loop end patches 177 facing two hook end patches 176 sewn onto pouch 170 and to support pouch 170 thereon. Strap 164 is longer than pouch 170 and formed so as to extend around a torso of human 2, and to be wrapped and secured thereabout. Thus, mesh layer 180 is the side of pouch 170 that is applied to target 1 (the human's back) while insulating layer 200 is exposed to environment 7 indirectly via pack system 160. Thus, heat flow 131 is designed and desired to flow primarily from target 1, through mesh layer 80, and into cooling media 30 (at its interior face 31) within pouch 70, and not from environment 7 and through insulating layer 100, and into cooling media 30 (at its exterior face 32).

The invention claimed is:

1. A cold pack, for being cooled and used to cool other materials comprising:

one or more cooling media, and a sealed package retaining said one or more cooling media;

said one or more cooling media each comprising a support structure and a liquid portion;

said liquid portion comprising a mixture of about 4 parts water::1 part isopropyl alcohol;

said mixture further comprising methyl salicylate.

2. The cold pack of claim 1, said support structure comprising one or more pieces of material containing interconnected volumes.

3. The cold pack of claim 2, said material containing interconnected volumes comprising cells that are partly open and that partly separate the volume in one cell from the volume in another cell.

4. The cold pack of claim 1, said support structure being selected from the group composed of sponge, spongy foam, open-cell foam, polyurethane craft foam, and synthetic sponge.

5. The cold pack of claim 1, said support structure comprising cells, each cell comprising a volume;

said cells partly separating the volume in cells from the volume in other cells; and said cells connected to other cells by flexible ligaments.

6. The cold pack of claim 1, said cooling media remaining malleable when said liquid portion is frozen.

7. A pack system for supporting and applying a cooling device, comprising:

at least two pouches;

each of said pouches comprising a mesh layer and an insulating layer; and at least one cold pack in each of said pouches, the cold packs comprising:

one or more cooling media, and a sealed package retaining said one or more cooling media;

said one or more cooling media each comprising a support structure and a liquid portion;

said liquid portion comprising a mixture of about 4 parts water::1 part isopropyl alcohol; and said mixture further comprising methyl salicylate.

8. The pack system of claim 7, said insulating layer comprising:

two layers of fabric, and a high-resistance layer interposed between said two fabric layers.

9. The pack system of claim 7, said insulating layer comprising:

a composite material comprising metallic foil and bubble insulation.

10. The pack system of claim 9, said composite material comprising:

two layers of a bubble material sandwiched between exterior layers of metallic foil.

11. The pack system of claim 7, said mesh layer comprising a layer of a rubberized mesh.

12. The pack system of claim 11, said rubberized mesh comprising alternating open sections, closed sections, and a grid; and said grid connecting said closed sections to other said closed sections.

13. The pack system of claim 7, said mesh layer comprising a polyester scrim coated with thermally-foamed PVC.

14. The pack system of claim 7, said insulating layer comprising a composite material including metallic foil layers and bubble insulation; and said mesh layer comprising a layer of a rubberized mesh.

15. The pack system of claim 7, comprising at least four pouches, said at least four pouches arranged in a grid.

16. The pack system of claim 15, comprising hook-and-loop fasteners for wrapping said pack system around the leg of a horse.

17. The pack system of claim 7, comprising one pouch; and further comprising an elastic band;

said elastic band joined to said pouch by an attachment.

* * * * *